United States Patent [19]

Phillion

[11] Patent Number: 4,734,517

[45] Date of Patent: Mar. 29, 1988

[54] N-PHOSPHONOMETHYLAMINOMETHYL-BORONIC ACID DERIVATIVES

[75] Inventor: Dennis P. Phillion, St. Charles, Mo.

[73] Assignee: Monsanto Company, St. Louis, Mo.

[21] Appl. No.: 922,927

[22] Filed: Oct. 24, 1986

[51] Int. Cl.$^4$ ................................................ C07F 9/00
[52] U.S. Cl. .................................................... 558/072
[58] Field of Search .......................................... 558/72

[56] References Cited

U.S. PATENT DOCUMENTS 3,013,046 12/1961 Denny et al. ..................... 558/72

Primary Examiner—Anton H. Sutto
Attorney, Agent, or Firm—Howard C. Stanley; David Bennett

[57] ABSTRACT

Certain novel esters of N-phosphonomethylaminomethylboronic acid are found to exhibit herbicidal properties.

5 Claims, No Drawings

N-PHOSPHONOMETHYLAMINOMETHYLBORONIC ACID DERIVATIVES

BACKGROUND OF INVENTION

The present invention relates to certain novel derivatives of N-phosphonomethylaminomethylboronic acid and specifically to certain esters of the acid.

The compounds of the present invention have not previously been described and are found to have significant herbicidal activity as is hereinafter demonstrated. Although sodium borate salts are known to be general herbicides, the herbicidal use of the novel boronate esters claimed herein has not been described.

DESCRIPTION OF THE INVENTION

The present invention provides novel boronate esters having the formula

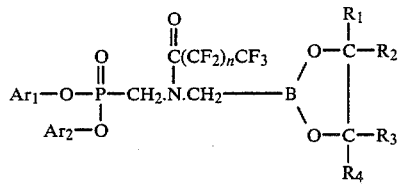

wherein each of $Ar_1$ and $Ar_2$ is an aryl or a substituted aryl group, n is an integer from 0 to 10 and $R_1$, $R_2$, $R_3$ and $R_4$ are each independently hydrogen or methyl groups.

In preferred compounds according to the invention both the groups $Ar_1$ and $Ar_2$ are phenyl groups, optionally substituted with $C_1$-$C_4$ alkyl or halogen radicals such as methyl, tert-butyl and chloro.

The fluorocarbonyl group $—(CF_2)_n—$ can have a value of "n" ranging from 0 to 10 but lower values such as 0 or 1 are preferred.

The preferred compounds are those in which each of $R_1$, $R_2$, $R_3$ and $R_4$ is methyl as this improves the stability of the ester.

The compounds of the present invention can be prepared by reaction of the appropriate N-fluoroacyl derivative of aminomethylphosphonic acid with sodium hydride and the appropriate pinacol iodomethylboronate ester in solution in dimethylformamide. The preparation of the pinacol boronate ester is described in The Journal of Organic Chemistry, 1986, 51 1610. The process by which the compounds can be made is more specifically described in the following examples which are for the purpose of illustration only and are not intended to imply any limitation on the essential scope of the invention.

DESCRIPTION OF THE PREFERRED EMBODIMENTS

EXAMPLE I

This Example describes the production of a boronate ester having the formula:

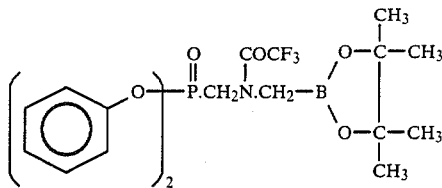

The above compound is made by the reaction of pinacol iodomethaneboronate with diphenyl N-trifluoroacetylaminomethylphosphonate which is itself prepared as follows:

A suspension of the hydrochloride salt of diphenyl aminomethylphosphonate (diphenyl AMPA.HCl), (10 g, 1 equivalent) and triethylamine (14 mL, 3 eq.) in 70 mL of toluene was stirred at room temperature for about 20 minutes. The resulting slurry was filtered to remove the triethylamine hydrochloride, then was cooled with an ice bath while 5.2 mL (1.1 eq.) of trifluoroacetic anhydride were slowly added with stirring. The resulting mixture was stirred at room temperature overnight. After extraction and drying, 8.1 g of light yellow crystals were obtained. Analysis showed this product to be diphenyl N-trifluoroacetylaminomethylphosphonate.

To a stirred suspension of sodium hydride (NaH) (0.10 g, 4.2 mmol) in dimethylformamide (5 mL) cooled with an ice-water bath was added diphenyl-N-trifluoroacetylaminomethylphosphonate (1.0 g, 2.8 mmol) in a single portion. To the resulting amide anion solution was added dropwise a solution of pinacol iodomethaneboronate (0.89 g, 3.3 mmol) in dimethylformamide (5 mL). The reaction mixture was warmed to ambient temperature and stirred for one hour, then was filtered to remove any remaining NaH. The filtrate was diluted with chloroform and thoroughly extracted with water, then it was dried over magnesium sulfate and concentrated to afford 1.04 g (74%) of the desired compound as a pale yellow oil.

EXAMPLE 2

This Example describes the production of a compound according to the invention having the formula:

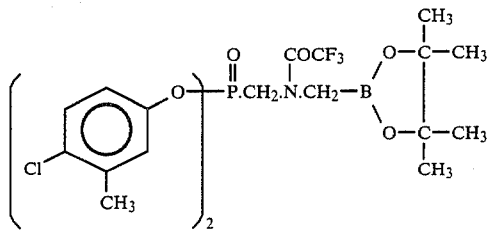

A solution of bis(4-chloro-3-methylphenyl)phosphite (250 mmol) and N,N,N-tribenzylhexahydrotriazine (29.85 g, 83.4 mmol) in benzene (170 mL) was refluxed for 3h, then cooled and allowed to stand at room temperature for three days. The resulting reaction mixture was concentrated and chromatographed on a Water's Prep 500A (eluted with 2:9 ethyl acetate/cyclohexane) to afford the free amine as an oil. Bubbling HCl gas through a diethyl ether solution of this oil cooled with an ice-water bath afforded 6.7 g (86%) of phosphonic acid, ([(trifluoroacetyl)amino]methyl)-, bis(4-chloro-3-methylphenyl) ester as a white solid.

Activated carbon (2 g) was added to a solution of the above bis ester (20 g, 41 mmol) in acetic acid (60 mL). The mixture was heated to 60°-70° C. for 30 min, then filtered through celite to remove the carbon. This procedure was repeated twice more to remove all the phosphorus impurities, then the product was hydrogenated (Parr apparatus) over 10% palladium on carbon (1 g). Often during these types of hydrogenations, the Pd/C catalyst was poisoned part way through the reaction. When this occurred, the reaction mixture was filtered through celite and the hydrogenation resumed with fresh catalyst. Upon theoretical $H_2$ uptake, the reaction mixture was filtered through celite and concentrated in vacuo to an oil. All traces of acetic acid were removed by stripping the material from toluene several times, then was dried in vacuo overnight to afford bis(4-chloro-3-methylphenyl) aminomethanephosphonate hydrochloride as an amorphous, white solid.

Triethylamine (10.6 mL, 76 mmol) was added in a single portion to a mechanically stirred suspension of bis(4-chloro-3-methylphenyl) aminomethanephosphonate hydrochloride (10.0 g, 25.2 mmol) in toluene (75 mL). After 20 minutes the slurry was filtered through celite, and the filtrate cooled with an ice-water bath while neat trifluoroacetic anhydride (4.4 mL, 31.2 mmol) was added dropwise. The resulting solution was warmed to room temperature and stirred for 1 hour, then was extracted with 10% aqueous HCl followed by saturated aqueous sodium bicarbonate. The toluene solution was dried over anhydrous magnesium sulfate, concentrated, and chromatographed on the Water's Prep 500A (eluted with 1:3 ethyl acetate/cyclohexane) to afford 6.74 g (59%) of bis(4-chloro-3-methylphenyl)-N-trifluoroacetyl aminomethanephosphonate as a pale yellow oil.

A solution of this oil (2.92 g, 6.4 mmol) and pinacol iodomethaneboronate (2.1 g, 7.8 mmol) in tetrahydrofuran (15 mL) was added dropwise to an ice-water cooled mixture of sodium hydride (0.25 g, 10.4 mmol) in tetrahydrofuran (10 mL). When $H_2$ evolution slowed, the reaction mixture was warmed to room temperature and stirred overnight. The reaction mixture was filtered to remove the excess sodium hydride, then was diluted with cyclohexane, extracted with saturated aqueous sodium bicarbonate, dried over magnesium sulfate, and concentrated to an oil. The excess pinacol iodomethaneboronate was removed by reaction of the oil with triethylamine (1.8 mL) in cyclohexane (20 mL) for four days. This solution was extracted with 10% aqueous HCl followed by saturated aqueous sodium bicarbonate, then was dried over magnesium sulfate and concentrated to afford the pure target compound as an oil.

EXAMPLE 3

This Example described the production of a compound according to the invention having the formula:

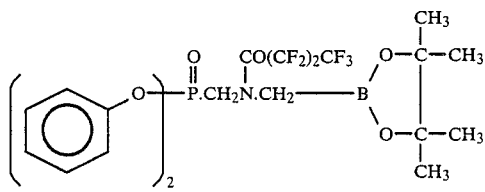

This is obtained by the reaction of pinacol iodomethaneboronate with diphenyl N-(n-heptafluorobutyryl) aminomethanephosphonate which is itself obtained in a manner analogous to that described in Example 1, with the substitution of $(C_3F_7CO)_2O$ for the $(CF_3CO)_2O$ used in Example 1.

A solution of diphenyl N-(n-heptafluorobutyryl) aminomethanephosphonate(3.85 g, 8.4 mmol) in tetrahydrofuran (10 mL) was added dropwise to an ice-water cooled mixture of sodium hydride (0.5 g, 12.5 mmol) in tetrahydrofuran (10 mL). When $H_2$ evolution slowed, the reaction mixture was warmed to room temperature until gas evolution ceased, then again cooled with an ice-water bath while a solution of pinacol iodomethaneboronate (2.70 g, 10.1 mmol) in tetrohydrofuran (5 mL) was added dropwise. The resulting solution was slowly allowed to warm to room temperature, and was monitored to completion by $^{31}P$ NMR. Excess sodium hydride was removed by filtration of the reaction mixture through celite, then the filtrate was diluted with diethyl ether and extracted with $H_2O$, dried over magnesium sulfate, and concentrated to afford 4.4 g (87%) of the desired compound as a red oil.

EXAMPLE 4

This Example describes a process for the production of a compound according to the invention having the formula:

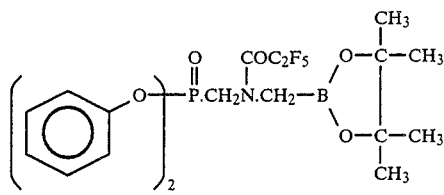

This compound was prepared by the reaction of pinacol iodomethaneboronate with diphenyl N-(pentafluoropropionyl)aminomethanephosphonate which is itself obtained in a manner analogous to that described in Example 1 with the substitution of $(C_2F_5CO)_2O$ for the $(CF_3CO)_2O$ used in Example 1.

This phosphonate ester (3.0 g, 7.3 mmol) is reacted with pinacol iodomethaneboronate (2.36 g, 8.8 mmol), NaH (0.26 g, 10.8 mmol), and DMF (20 mL) in the manner described in Example 1 to afford 3.50 g (87%) of the desired compound as a pale yellow oil.

EXAMPLE 5

This Example describes the production of a compound according to the invention having the formula:

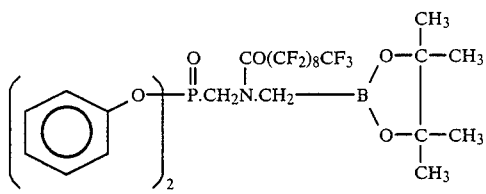

This compound was prepared by the reaction of pinacol iodomethaneboronate with diphenyl N-(n-perfluorodecanoyl)aminomethanephosphonate. The preparation of this phosphonate ester is first described Phosphorus pentachloride ($PCl_5$), (10.53 g, 50 mmol) was added in small portions to perfluorodecanoic acid (25 g, 49 mmol). Although the ensuing reaction was not too exothermic, HCl gas evolution was vigorous. The resulting solution was refluxed for three hours then a second portion of PCl$_5$ (10.53 g, 50 mmol) was added and the mixture refluxed an additional two hours. Distillation afforded 18.25 g (70%) of perfluorodecanoyl chloride as a colorless liquid.

Triethylamine (14.4 mL, 103 mmol) was added dropwise to an ice-water cooled suspension of diphenyl aminomethanephosphonate hydrochloride (10.3 g, 34.4 mmol) in toluene (75 mL). This mixture was stirred for 20 min, then filtered through celite to remove the triethylamine hydrochloride. The filtrate was cooled with an ice-water bath while perfluorodecanoyl chloride (18.25 g, 34.3 mmol) was added dropwise. The resulting reaction mixture was stirred at room temperature overnight, then was diluted with toluene and extracted with 10% aqueous HCl, followed by saturated aqueous sodium bicarbonate. The toleune solution was dried over magnesium sulfate, concentrated, and chromatographed on a Water's Prep 500A (eluted with 23:77 ethyl acetate/cyclohexane) to afford 5.44 g (21%) of diphenyl N-(n-perfluorodecanoyl)aminomethanephosphonate as a white solid.

A solution of the above phosphonate (3.24 g, 4.3 mmol) in tetrahydrofuran (15 mL) was added dropwise to an ice-water cooled mixture of sodium hydride (0.17 g, 7.1 mmol) in tetrahydrofuran (5 mL). The reaction mixture became so frothy that additional tetrahydrofuran (10 mL) was added. The cooling bath was removed and after one hour, a solution of pinacol iodomethaneboronate (1.37 g, 5.1 mmol) in tetrahydrofuran (5 mL) was added to the amide anion. The resulting mixture was stirred at room temperature overnight, then was filtered to remove excess sodium hydride. The filtrate was diluted with diethyl ether and thoroughly extracted with saturated aqueous sodium bicarbonate followed by water, then was dried over magnesium sulfate and concentrated to an oil. The cyclohexane soluble portion of this oil was filtered through silicic acid (eluted with CH$_3$CN), then was filtered through celite and concentrated in vacuo to afford 2.53 g of the desired compound as a waxy solid.

EXAMPLE 6

This Example describes the preparation of a compound according to the invention having the formula:

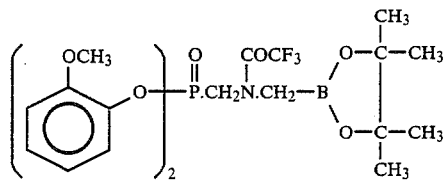

This compound was formed by the reaction of pinacol iodomethaneboronate with Bis(2-methoxyphenyl)-N-trifluoroacetyl)aminomethanephosphonate. The preparation of this phosphonate is first described.

A solution of bis(2-methoxyphenyl)phosphite (17.8 g, 60 mmol) and N,N,N-tribenzylhexahydrotriazine (7.2 g, 20 mmol) in benzene (40 mL) was refluxed for 3 hours, then cooled and allowed to stand at room temperature for 3 days. The resulting reaction mixture was concentrated to an oil, then dissolved in diethyl ether and cooled with an ice-water bath while HCl gas was bubbled through. The precipitate which formed was collected to afford 24 g (89%) of bis(2-methoxyphenyl) aminomethanephosphonate hydrochloride hydrate (1:0.5) as a very hydroscopic white solid.

In the same fashion as descried in Example 2 the above phosphonate (20 g, 44 mmol) was purified over activated carbon, then hydrogenated over Pd/C (1 g). A mixture of the resulting bis(2-methoxyphenyl) aminomethanephosphonate hydrochloride (21.2 g, 59 mmol), triethylamine (18.7 mL, 134 mmol), trifluoroacetic anhydride (7.6 mL, 54 mmol) and toluene (125 mL) were then combined, and purified on a Water's Prep 500A (eluted with 2:3 ethyl acetate/hexane) to afford 4.71 g (21%) of bis(2-methoxyphenyl)-N-(trifluoroacetyl)-aminomethanephosphonate A solution of the above amide (5.0 g, 11.9 mmol) and pinacol iodomethaneboronate (3.2 g, 11.9 mmol) in tetrahydrofuran (20 mL) was added dropwise to an ice-water cooled mixture of sodium hydride (0.5 g, 20.8 mmol) in tetrahydrofuran (20 mL). When H$_2$ evolution slowed, the reaction mixture was warmed to room temperature and stirred overnight. The reaction mixture was filtered to remove the excess sodium hydride, diluted with cyclohexane and extracted with saturated aqueous sodium bicarbonate, and then dried over magnesium sulfate and concentrated to afford 5.14 g (77%) of the target compound as a pale yellow oil.

EXAMPLE 7

The post-emergence herbicidal activity of the compounds of this invention was demonstrated by greenhouse testing in the following manner. A good grade of top soil is placed in aluminum pans having holes in the bottom and compacted to a depth of 0.95 to 1.27 cm from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks) each pan, except for the control pans, is removed individually to a spraying chamber and sprayed by means of an atomizer operating at a positive air pressure of approximately 1.46 kg/cm$^2$ absolute. The atomizer contains 6 mL of a solution or suspension of the chemical. In that 6 mL is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0by weight stock solution or suspension of the candidate chemical in an organic solvent, such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded.

The post-emergence herbicidal activity index used in Tables I and II is as follows:

| Plant Response | Index |
| --- | --- |
| less than 25% inhibition | 0 |
| 25 to less than 50% inhibition | 1 |
| 50 to less than 75% inhibition | 2 |
| 75 to 99% inhibition | 3 |
| 100% inhibition (complete kill) | 4 |

The plant species utilized in these tests are identified by letter in accordance with the following legend:

| | |
| --- | --- |
| A - Canada Thistle* | K - Barnyardgrass |
| B - Cocklebur | L - Soybean |
| C - Velvetleaf | M - Sugar Beet |
| D - Morning Glory | N - Wheat |
| E - Lambsquarters, Common | O - Rice |
| F - Smartweed, Pennsylvania | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass, Large |

*Established from vegetative propagules.
A "—" in the tables indicates that the particular species was absent in the test.

manner by combining them with other materials which are wel known in the herbicide art. The following is a description of herbicidal compositions employing the herbicidal compounds of this invention together with known materials and formulations typically utilized in the herbicide art.

The herbicidal compositions, including concentrates which require dilution prior to application to the plants, of this invention contain from 5 to 95 parts by weight of at least 1 compound of this invention and from 5 to 95 parts by weight of an adjuvant in liquid or solid form, for example, from about 0.25 to 25 parts by weight of wetting agent, from about 0.25 to 25 parts by weight of a dispersant, and, from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least 1 compound of this invention, together with the adjuvants. Where required, from about 0.1 to 2.0 parts by weight of the inert liquid extender can be replaced by a corrosion inhibitor, such as ethanol mercaptan, sodium thiosulfate, dodecylmono or dimercaptan, or antifoaming agent, such as a dimethylpolysiloxane or both. The compositions are prepared by admixing the active ingredient with an adjuvant including diluents, extenders, carriers, and

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| 1 | 2 | 11.2 | — | 2 | 1 | 2 | 1 | 2 | 0 | 0 | 0 | 1 | 2 |
|   | 4 |      | — | 2 | 1 | 2 | 2 | 3 | 0 | 1 | 0 | 1 | 1 |
| 2 | 2 | 11.2 | 0 | 1 | 0 | 1 | 0 | 0 | 0 | 0 | 0 | 0 | 1 |
| 3 | 2 | 11.2 | 0 | 2 | 1 | 1 | 1 | 1 | 0 | 0 | 1 | 0 | 1 |
|   | 4 |      | 0 | 2 | 1 | 1 | 1 | 1 | 0 | 0 | 1 | 0 | 1 |
| 4 | 2 | 11.2 | — | 2 | 1 | 2 | 1 | 2 | 0 | 1 | 2 | 1 | 1 |
|   | 4 |      | — | 3 | 1 | 2 | 1 | 2 | 0 | 2 | 2 | 1 | 1 |
| 5 | 2 | 11.2 | 0 | 2 | 0 | 1 | 0 | 0 | 0 | 0 | 0 | 0 | 0 |
|   | 4 |      | 0 | 2 | 0 | 1 | 0 | 0 | 0 | 0 | 0 | 0 | 0 |
| 6 | 2 | 11.2 | 1 | 1 | 0 | 1 | 1 | 0 | 1 | 0 | 0 | 0 | 0 |
|   | 4 |      | 1 | 1 | 1 | 2 | 1 | 1 | 1 | 0 | 0 | 0 | 0 |

TABLE II

| Compound of Example No. | WAT | kg/h | L | M | N | O | P | B | Q | D | R | E | F | C | H | S | K | T |
| --- | --- | --- | --- | --- | --- | --- | --- | --- | --- | --- | --- | --- | --- | --- | --- | --- | --- | --- |
| 1* | 2 | 5.6 | 1 | 1 | 0 | 0 | 0 | 3 | 2 | 2 | 1 | 3 | 3 | 2 | 0 | 0 | 0 | 0 |
|    | 4 |     | 1 | 0 | 4 | 0 | 0 | 3 | 0 | 0 | 0 | 3 | 2 | 2 | 0 | 0 | 0 | 2 |
|    | 2 | 1.12 | 1 | 1 | 0 | 0 | 0 | 3 | 1 | 2 | 0 | 2 | 2 | 2 | 0 | 0 | 0 | 0 |
|    | 4 |      | 0 | 1 | 4 | 0 | 0 | 2 | 1 | 1 | 0 | 2 | 1 | 1 | 0 | 1 | 0 | 2 |
| 4  | 2 | 5.6 | 2 | 2 | 2 | 0 | 2 | 3 | 2 | 2 | 2 | 2 | 2 | 2 | 0 | 0 | 2 | 2 |
|    | 4 |     | 3 | 2 | 0 | 0 | 0 | 3 | 3 | 3 | 1 | 3 | 2 | 3 | 0 | 0 | 1 | 2 |
|    | 2 | 1.12 | 1 | 1 | 1 | 0 | 0 | 1 | 1 | 0 | 0 | 0 | 0 | 0 | 0 | 0 | 0 | 0 |

*Sprayed in 100 GPA tetrahydrofuran; 1% solution was 2 weeks old.

From the test results presented in Tables I and II, it can be seen that the post-emergent herbicidal activity of the compounds of this invention is general in nature. In this regard it should be recognized that each individual species selected for the above tests is a representative member of a recognized family of plant species.

Typically, herbicidal compounds of this invention are provided in the form of concentrates which require dilution prior to application to plants. The usual means for diluting the herbicide is the preparation of herbicidal compositions wherein the compound possessing herbicidal activity is mixed with other materials. Such other materials may be in either liquid or solid form and comprise adjuvants, inert materials, etc.

The herbicidal composition containing herbicidal compounds of this invention are prepared in the usual conditioning agents to provide compositions in the form of finely-divided particulate solids, pellets, solutions, dispersions, or emulsions. Thus, the active ingredient can be used with an adjuvant, such as a finely-divided solid, a liquid of organic origin, water, a wetting agent, a dispersing agent, an emulsifying agent, or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents, and emulsifying agents are included therein. Anionic, cationic, and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, polyoxyethylene derivatives of phenols and alkyl-phenols (particularly isooctylphenol and nonylphenol), and polyoxyethylene derivatives of the mono-higher fatty acid esters of hexitol anhydrides (e.g., sorbitan). Preferred dispersants are methyl cellulose, polyvinyl alcohol, sodium lignosulfonates, polymeric alkyl naphthalene sulfonates, sodium naphthalene sulfonate, polymethylene bisnaphthalenesulfonate, and sodium N-methyl-N-(long chain acid)laurates.

When operating in accordance with the present invention, effective amounts of the compounds or compositions of this invention are applied to the plants or are incorporated into aquatic media in any convenient fashion. The application of liquid and particulate solid compositions to plants or soil can be carried out by conventional methods, e.g., power dusters, boom and hand sprayers, and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors, as the plant species and stage of development thereof, and the amount of rainfall as well as the specific compound employed. In foliar treatment for the control of vegetative growth, the active ingredients are applied in amounts from about 0.112 to about 56.0 or more kilograms per hectare. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof, and the like. These forms may be assembled in any manner desired including a pipe rope wick, a wedge rope wick, a multi-rope wick, and the like.

In another possible application method, liquid compositions may be selectively applied to weeds by the use of recirculating sprayer systems wherein the recirculating spray unit is mounted on a tractor or high clearance mobile equipment, and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in "Innovative Methods of Post-Emergence Weed Control", McWhorter, C. G., Southern Weed Science Society, 33rd Annual Meeting Proceedings, Jan. 15–17, 1980; Auburn University Printing Service, Auburn, Alabama, U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator - Tool With A Future", Dale, James E., pp. 3–4; "The Recirculating Sprayer and Roundup Herbicide", Derting, Claude W., pp. 5–7; and "C.D.A. Herbicide Application", McGarvey, Frank X., *Weeds Today*, Volume 11, Number 2, pp. 8–9, Late Spring, 1980, 309 W. Clark St., Champaign, Illinois, U.S.A., the teachings of which are incorporated herein by reference in their entirety.

Although this invention has been described with respect to specific modifications, the details thereof are not to be construed as limitations for it will be apparent that various equivalents, changes, and modifications may be resorted to without departing from the spirit and scope thereof, and it is understood that such equivalent embodiments are intended to be included herein.

What is claimed is:

1. A Compound having the formula:

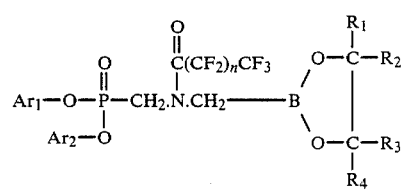

wherein each of $Ar_1$ and $Ar_2$ is an aryl or a halo- or $C_1$ to $C_4$ alkyl substituted aryl group, n is an integer from 0 to 10, and $R_1$, $R_2$, $R_3$ and $R_4$ are each independently hydrogen or methyl groups.

2. A compound according to claim 1 in which n is 0 or 1.

3. A compound according to claim 1 in which each of $R_1$, $R_2$, $R_3$ and $R_4$ are methyl groups.

4. A compound according to claim 1 in which n=0 and $R_1$, $R_2$, $R_3$ and $R_4$ are methyl groups.

5. A compound having the formula:

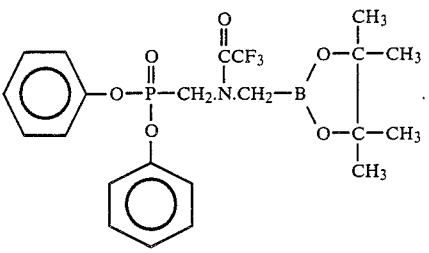

* * * * *